US009005270B2

(12) United States Patent
Perkins et al.

(10) Patent No.: US 9,005,270 B2
(45) Date of Patent: Apr. 14, 2015

(54) HIGH METAL TO VESSEL RATIO STENT AND METHOD

(75) Inventors: Keith Perkins, Santa Rosa, CA (US);
Samuel Robaina, Santa Rosa, CA (US);
Jeffery Argentine, Petaluma, CA (US);
Walter Bruszewski, Windsor, CA (US);
Andrew Kiehl, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 299 days.

(21) Appl. No.: 13/430,942

(22) Filed: Mar. 27, 2012

(65) Prior Publication Data
US 2013/0261728 A1    Oct. 3, 2013

(51) Int. Cl.
A61F 2/82      (2013.01)
A61F 2/915     (2013.01)

(52) U.S. Cl.
CPC ....... *A61F 2/915* (2013.01); *A61F 2002/91525* (2013.01)

(58) Field of Classification Search
USPC .................................................. 623/1.1–1.19
See application file for complete search history.

(56) References Cited

U.S. PATENT DOCUMENTS

| 5,800,526 | A  | 9/1998  | Anderson et al. |
| 5,817,126 | A  | 10/1998 | Imran |
| 5,817,152 | A  | 10/1998 | Birdsall et al. |
| 6,093,199 | A  | 7/2000  | Brown et al. |
| 6,152,956 | A  | 11/2000 | Pierce |
| 6,190,402 | B1 | 2/2001  | Horton et al. |
| 6,270,524 | B1 | 8/2001  | Kim |
| 6,344,052 | B1 | 2/2002  | Greenan et al. |
| 6,451,051 | B2 | 9/2002  | Drasler et al. |
| 7,069,835 | B2 | 7/2006  | Nishri et al. |
| 7,093,527 | B2 | 8/2006  | Rapaport et al. |
| 7,275,471 | B2 | 10/2007 | Nishri et al. |
| 7,306,624 | B2 | 12/2007 | Yodfat et al. |
| 7,331,987 | B1 | 2/2008  | Cox |
| 7,572,290 | B2 | 8/2009  | Yodfat et al. |
| 7,588,597 | B2 | 9/2009  | Frid |

(Continued)

FOREIGN PATENT DOCUMENTS

| EP | 1302179 | 4/2003 |
| EP | 1621159 | 2/2006 |

(Continued)

OTHER PUBLICATIONS

Kallmes, et al., "A New Endoluminal, Flow-Disrupting Device for Treatment of Saccular Aneurysms" Stroke, pp. 2346-2352, Aug. 2007.

(Continued)

*Primary Examiner* — Suzette J Gherbi

(57) ABSTRACT

A method includes covering ostai of branch vessels emanating from a main vessel and an aneurysm with a high metal to vessel ratio stent. A metal to vessel ratio of the high metal to vessel ratio stent is sufficiently high to encourage tissue ingrowth around the high metal to vessel ratio stent yet is sufficiently low to ensure perfusion of the branch vessels through the high metal to vessel ratio stent. The ingrowth of tissue provides secure fixation and sealing of the high metal to vessel ratio stent to the main vessel and remodels and essentially eliminates the aneurysm. Further, as the entire high metal to vessel ratio stent is permeably, the high metal to vessel ratio stent is deployed without having to rotationally position the high metal to vessel ratio stent.

29 Claims, 14 Drawing Sheets

(56) References Cited

U.S. PATENT DOCUMENTS

| | | | |
|---|---|---|---|
| 7,828,834 B2 | 11/2010 | Garbe | |
| 8,439,964 B2* | 5/2013 | McNamara et al. | 623/1.15 |
| 2002/0013616 A1 | 1/2002 | Carter et al. | |
| 2002/0156525 A1* | 10/2002 | Smith et al. | 623/1.22 |
| 2003/0109917 A1 | 6/2003 | Rudin et al. | |
| 2003/0130720 A1 | 7/2003 | DePalma et al. | |
| 2003/0176914 A1* | 9/2003 | Rabkin et al. | 623/1.15 |
| 2003/0204244 A1 | 10/2003 | Stiger | |
| 2004/0215312 A1 | 10/2004 | Andreas | |
| 2004/0267352 A1 | 12/2004 | Davidson et al. | |
| 2005/0131524 A1 | 6/2005 | Majercak | |
| 2005/0177224 A1 | 8/2005 | Fogarty et al. | |
| 2007/0010872 A1 | 1/2007 | Gregorich | |
| 2007/0168018 A1 | 7/2007 | Amplatz et al. | |
| 2007/0265695 A1 | 11/2007 | Majercak | |
| 2008/0167707 A1* | 7/2008 | Marrey et al. | 623/1.16 |
| 2008/0208319 A1* | 8/2008 | Rabkin et al. | 623/1.16 |
| 2009/0234429 A1 | 9/2009 | Lau | |
| 2009/0259292 A1 | 10/2009 | Bonhoeffer | |
| 2009/0270970 A1 | 10/2009 | Yodfat et al. | |
| 2010/0010622 A1* | 1/2010 | Lowe et al. | 623/1.16 |
| 2010/0137673 A1* | 6/2010 | Srivastava et al. | 600/3 |
| 2010/0174358 A1* | 7/2010 | Rabkin et al. | 623/1.16 |
| 2010/0184507 A1 | 7/2010 | Gatto et al. | |
| 2010/0198334 A1 | 8/2010 | Yodfat et al. | |
| 2010/0217373 A1* | 8/2010 | Boyle et al. | 623/1.11 |
| 2010/0262217 A1 | 10/2010 | Bruszewski | |
| 2010/0274345 A1 | 10/2010 | Rust | |
| 2011/0093059 A1* | 4/2011 | Fischell et al. | 623/1.15 |
| 2011/0137407 A1* | 6/2011 | Nguyen et al. | 623/1.42 |
| 2012/0022508 A1 | 1/2012 | Gross et al. | |
| 2012/0029618 A1* | 2/2012 | Tischler et al. | 623/1.16 |
| 2012/0046734 A1* | 2/2012 | Girton | 623/1.42 |
| 2012/0071962 A1* | 3/2012 | Huang et al. | 623/1.16 |
| 2012/0095548 A1* | 4/2012 | Gregorich et al. | 623/1.46 |
| 2012/0239139 A1* | 9/2012 | Wnendt et al. | 623/1.42 |
| 2012/0271399 A1 | 10/2012 | Perkins et al. | |
| 2013/0261727 A1 | 10/2013 | Perkins et al. | |
| 2013/0261732 A1* | 10/2013 | Perkins et al. | 623/1.15 |
| 2013/0261735 A1* | 10/2013 | Pacetti et al. | 623/1.36 |
| 2013/0331927 A1* | 12/2013 | Zheng et al. | 623/1.19 |

FOREIGN PATENT DOCUMENTS

| | | |
|---|---|---|
| EP | 1652495 | 5/2006 |
| WO | 98/47447 A1 | 10/1998 |
| WO | WO98/47447 | 10/1998 |
| WO | 03/007840 A2 | 1/2003 |
| WO | WO03/007840 | 1/2003 |
| WO | WO2006/124824 | 11/2006 |
| WO | WO 2008/051554 | 5/2008 |
| WO | WO 2008/091515 | 7/2008 |
| WO | WO2009/137296 | 11/2009 |
| WO | WO2011/008989 | 1/2011 |
| WO | WO2011/012147 | 2/2011 |

OTHER PUBLICATIONS

Fiorella et al., "Definitive Reconstruction of Circumferential, Fusiform Intracranial Aneurysms With the Pipeline Embolization Device" neurosurgery, vol. 62, No. 5, May 2008, pp. 1115-1121.

Fiorella et al., "Curative Reconstruction of a giant Midbasilar Trunk Aneurysm with the Pipeline Embolization Device" Neurosurgery, vol. 64, No. 2, Feb. 2009, pp. 212-217.

* cited by examiner

HIGH METAL TO VESSEL RATIO STENT AND METHOD

BACKGROUND

1. Field

The present application relates to an intra-vascular device and method. More particularly, the present application relates to a device for treatment of intra-vascular diseases.

2. Description of the Related Art

A conventional stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

Stent-grafts with custom side openings are sometimes fabricated to accommodate the particular vessel structure of each individual patient. Specifically, as the location of branch vessels emanating from a main vessel, e.g., having the aneurysm, varies from patient to patient, stent-grafts are fabricated with side openings customized to match the position of the branch vessels of the particular patient. However, custom fabrication of stent-grafts is relatively expensive and time consuming.

Further, the stent-grafts must be deployed such that the custom side openings are precisely aligned with the respective locations of the branch vessels. This is a relatively complex procedure thus increasing the risk of the procedure.

SUMMARY

A method includes covering ostai of branch vessels emanating from a main vessel and an aneurysm with a high metal to vessel ratio stent. A metal to vessel ratio of the high metal to vessel ratio stent is sufficiently high to encourage tissue ingrowth around the high metal to vessel ratio stent yet is sufficiently low to ensure perfusion of the branch vessels through the high metal to vessel ratio stent. The ingrowth of tissue provides secure fixation and sealing of the high metal to vessel ratio stent to the main vessel (tissue remodeling) and essentially eliminates the aneurysm from the main vessel circulation. Further, as the entire high metal to vessel ratio stent is permeable, the high metal to vessel ratio stent is deployed without having to rotationally position the high metal to vessel ratio stent to allow for the perfusion of the target branch vessels as is currently done with branched and fenestrated devices.

These and other features of embodiments will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 16:
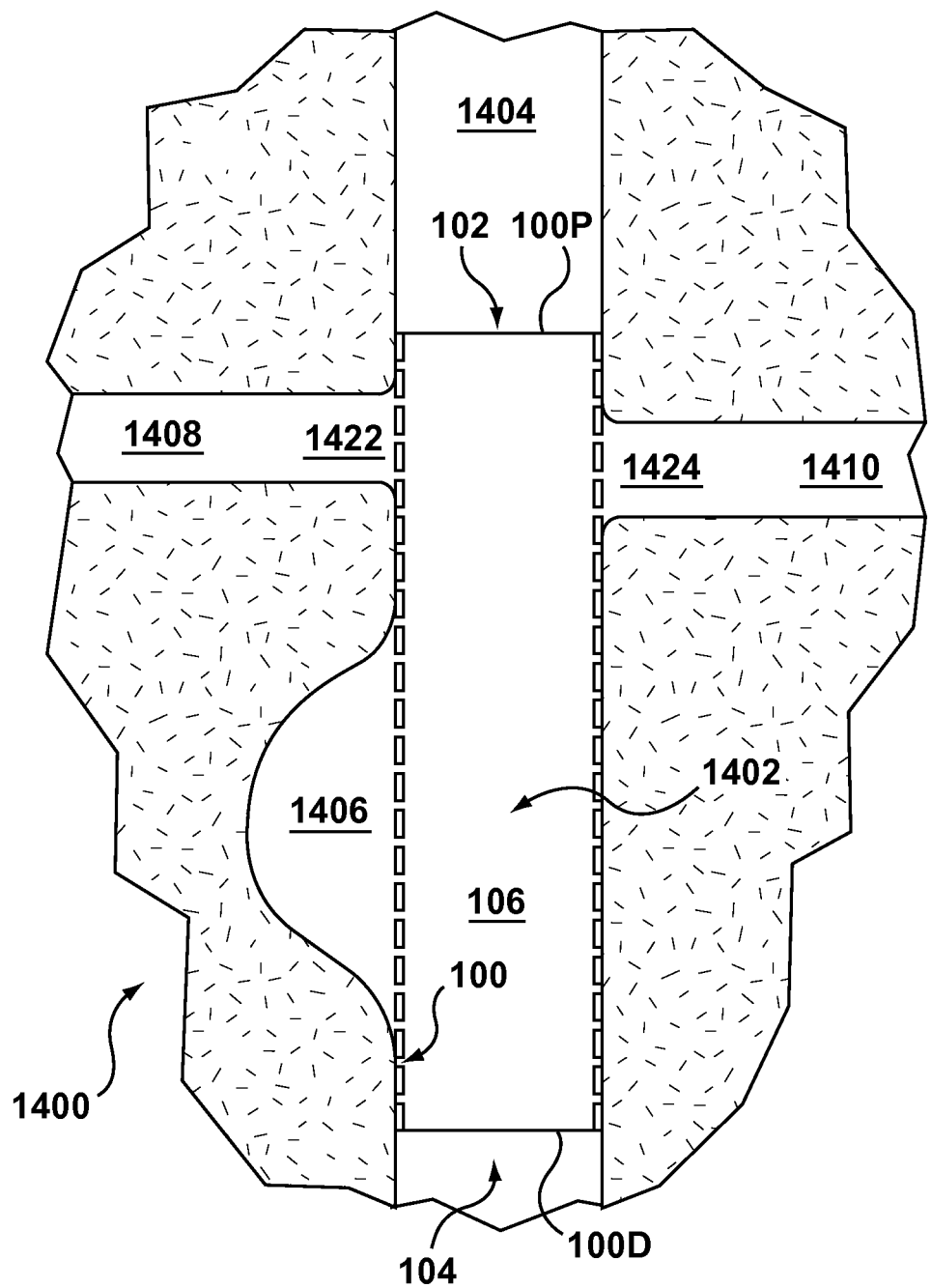
FIG. 16 is a cross-sectional view of the vessel assembly of FIGS. 14-15 after deployment of the high metal to vessel ratio stent of FIGS. 1 and 2 in accordance with one embodiment.

As an overview and in accordance with one embodiment, referring to FIG. 16, a method includes covering ostai 1422, 1424 of branch vessels 1408, 1410 emanating from a main vessel 1404 with a high metal to vessel ratio stent 100. A metal to vessel ratio of high metal to vessel ratio stent 100 is sufficiently high to encourage tissue ingrowth around high metal to vessel ratio stent 100 yet is sufficiently low to ensure perfusion of branch vessels 1408, 1410 through high metal to vessel ratio stent 100. The ingrowth of tissue provides secure fixation and sealing of high metal to vessel ratio stent 100 to main vessel 1404 thus minimizing the risk of endoleaks and migration.

Further, deployment of high metal to vessel ratio stent 100 is relatively simple thus minimizing the complexity and thus risk of deploying high metal to vessel ratio stent 100. More particularly, as the entire high metal to vessel ratio stent 100 is permeable, high metal to vessel ratio stent 100 is deployed without having to rotationally position high metal to vessel ratio stent 100 to be aligned with branch vessels 1408, 1410 as is currently done with deployment of branched and fenestrated devices.

Figure 17:
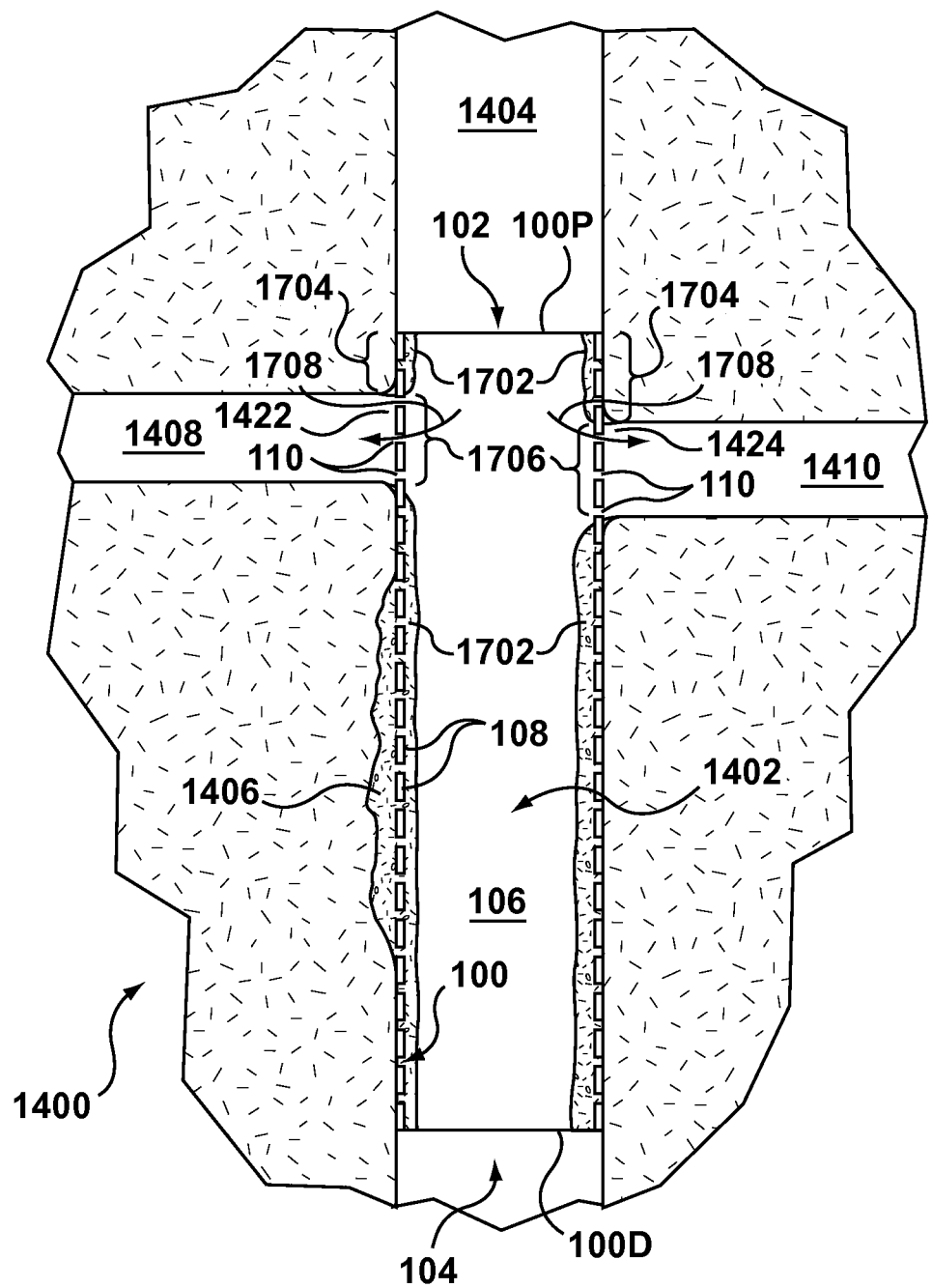
FIG. 17 is a cross-sectional view of the vessel assembly of FIG. 16 illustrating tissue ingrowth into the high metal to vessel ratio stent.

The method further includes covering and excluding an aneurysm 1406 of main vessel 1404 with high metal to vessel ratio stent 100. Referring now to FIGS. 16 and 17 together, the ingrowth of tissue 1702 restricts expansion of aneurysm 1406. In one embodiment, aneurysm 1406 is remodeled and essentially eliminated as illustrated in FIG. 17.

Figure 1:
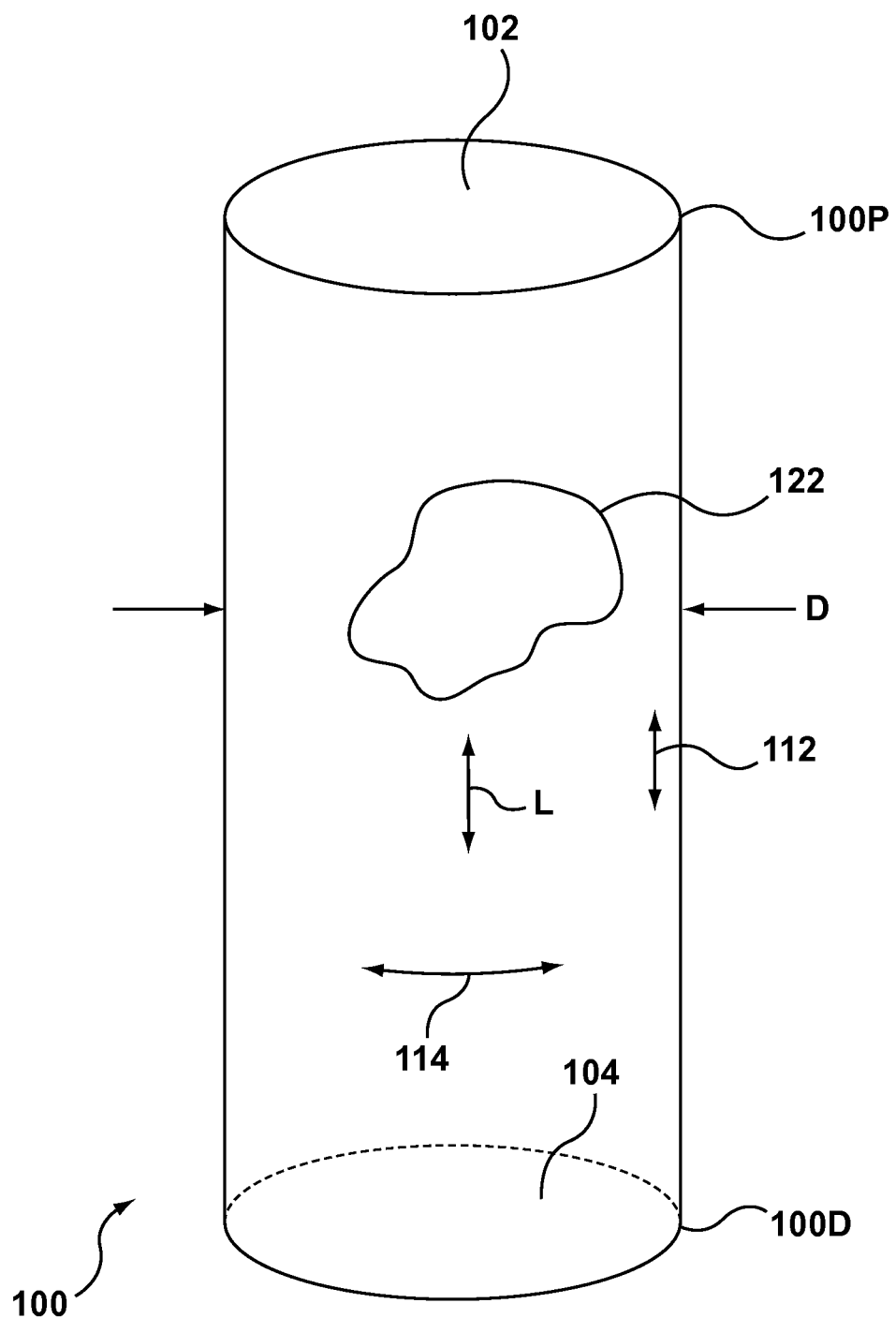
FIG. 1 is a perspective outline view of a high metal to vessel ratio stent in its final configuration in accordance with one embodiment.
Figure 2:
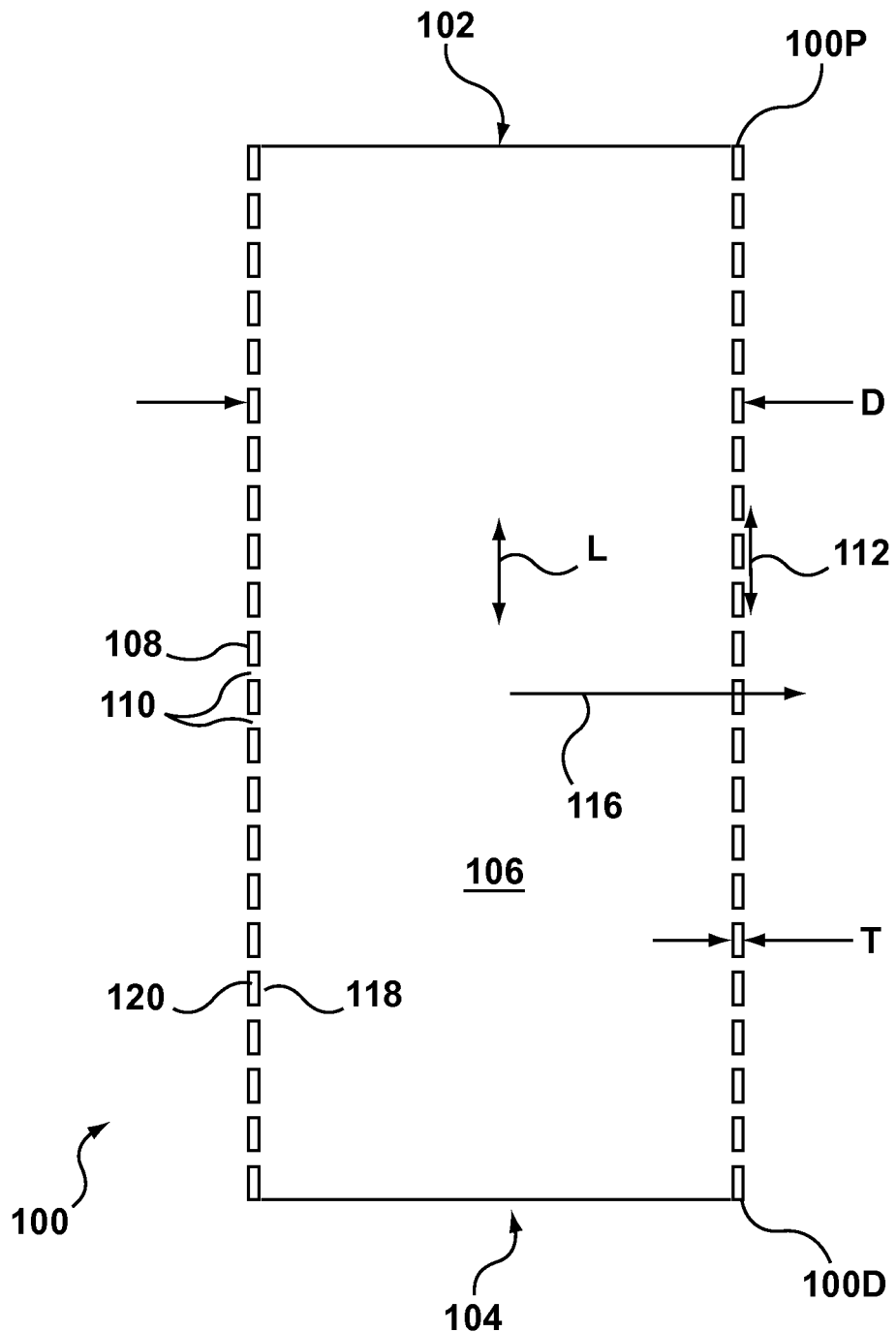
FIG. 2 is a cross-sectional view of the high metal to vessel ratio stent of FIG. 1.

Now in more detail, FIG. 1 is a perspective outline view of a high metal to vessel ratio stent 100, e.g., an abdominal aortic stent, in its final configuration in accordance with one embodiment. FIG. 2 is a cross-sectional view of high metal to vessel ratio stent 100 of FIG. 1. High metal to vessel ratio stent 100 is sometimes called an endoluminal flow disrupting device.

Referring now to FIGS. 1 and 2 together, high metal to vessel ratio stent 100 includes a proximal main opening 102 at a proximal end 100P of high metal to vessel ratio stent 100 and a distal main opening 104 at a distal end 100D of high metal to vessel ratio stent 100.

As used herein, the proximal end of a prosthesis such as high metal to vessel ratio stent 100 is the end closest to the heart via the path of blood flow whereas the distal end is the end furthest away from the heart during deployment. In contrast and of note, the distal end of the delivery system is usually identified to the end that is farthest from the operator (handle) while the proximal end of the delivery system is the end nearest the operator (handle).

For purposes of clarity of discussion, as used herein, the distal end of the delivery system is the end that is farthest from the operator (the end furthest from the handle) while the distal end of the prosthesis is the end nearest the operator (the end nearest the handle), i.e., the distal end of the delivery system and the proximal end of the prosthesis are the ends furthest from the handle while the proximal end of the delivery system and the distal end of the prosthesis are the ends nearest the handle. However, those of skill in the art will understand that depending upon the access location, the prosthesis and delivery system description may be consistent or opposite in actual usage.

High metal to vessel ratio stent 100 is cylindrical and includes a longitudinal axis L. A main lumen 106 is defined by high metal to vessel ratio stent 100 and extends generally parallel to longitudinal axis L and between proximal main opening 102 and distal main opening 104 of high metal to vessel ratio stent 100.

In accordance with this embodiment, high metal to vessel ratio stent 100 has a substantially uniform diameter D. However, in other embodiments, high metal to vessel ratio stent 100 has a non-uniform diameter.

High metal to vessel ratio stent 100 is a semi-permeable barrier made of patterned material 108, e.g., is a dense laser cut metal pattern. High metal to vessel ratio stent 100 includes patterned material 108 and a plurality of holes 110 through which fluid, e.g., blood, can pass. Generally, high metal to vessel ratio stent 100 is permeable, sometimes called porous, to fluid, i.e., fluid can pass through high metal to vessel ratio stent 100 and more particularly, through holes 110. This allows fluid, e.g., blood, to pass through high metal to vessel ratio stent 100 and nourish, e.g., with oxygen and nutrients, the covered vessel wall. In this manner, hypoxia of the covered vessel wall is avoided. Further, high metal to vessel ratio stent 100 is permeable to tissue ingrowth.

Longitudinal direction 112 is the direction along high metal to vessel ratio stent 100 parallel to longitudinal axis L. Circumferential direction 114 is the direction along the circumference of high metal to vessel ratio stent 100 in plane perpendicular to longitudinal axis L of high metal to vessel ratio stent 100. Radial direction 116 is along a radius extending from longitudinal axis L in plane perpendicular to longitudinal axis L of high metal to vessel ratio stent 100.

Generally, there are a plurality, e.g., three or more, of holes 110 arranged in both longitudinal direction 112 as well as circumferential direction 114.

The ratio of material 108 per unit area of high metal to vessel ratio stent 100 is high, e.g., greater than or equal 30%. This ratio is sometimes called the metal to vessel ratio (or metal to artery ratio) as it defines the percent of the vessel covered with material 108 per unit area of the vessel. Stated another way, the percentage of high metal to vessel ratio stent 100 formed by material 108 is high, e.g., greater than or equal to 30%, and the percentage of high metal to vessel ratio stent 100 formed of holes 110 is low, e.g., less than or equal to 70%.

Generally, the metal to vessel ratio is defined as the area occupied by material 108 of high metal to vessel ratio stent 100 for a unit area of high metal to vessel ratio stent 100 when in the final configuration. To illustrate, for an X square centimeter ($cm^2$) area of high metal to vessel ratio stent 100, Y percent is formed of material 108 whereas Z percent is formed of holes 110, where Y+Z=100. Continuing with this example, Y is the metal to vessel ratio expressed as percent.

To give a specific example for a 40% metal to vessel ratio, for a 1.0 square centimeter area of high metal to vessel ratio stent 100, 0.4 square centimeters would be covered by material 108 whereas 0.6 square centimeters would be covered by holes 110. The metal to vessel ratio can be expressed as a fraction, e.g., 0.4 for this example, or as a percentage, e.g., 40% for this example. To convert, the fraction is multiplied by 100 to obtain the percentage.

Although a fixed metal to vessel ratio is set forth, in other embodiments, the metal to vessel ratio of high metal to vessel ratio stent 100 varies in the longitudinal direction 112 and/or in the circumferential direction 114 along high metal to vessel ratio stent 100.

As set forth above, the metal to vessel ratio is defined when high metal to vessel ratio stent 100 is in the final configuration. High metal to vessel ratio stent 100 is in the final configuration when in its final unconstrained expanded state, sometimes called at nominal deployment. More particularly, when the diameter of high metal to vessel ratio stent 100 is approximately equal, e.g., 10% to 20% oversized, to the diameter of the vessel in which high metal to vessel ratio stent 100 is being deployed and high metal to vessel ratio stent 100 is at its natural unconstrained length at this diameter, high metal to vessel ratio stent 100 is in its final state. Generally, once deployed within the vessel at its natural unconstrained length as discussed below, high metal to vessel ratio stent 100 is in the final configuration.

The final configuration should be contrasted to the constrained configuration of high metal to vessel ratio stent 100. High metal to vessel ratio stent 100 is in a constrained configuration when high metal to vessel ratio stent 100 is constrained to a reduced diameter, e.g., within a delivery sheath. Further, high metal to vessel ratio stent 100 is in a constrained configuration when high metal to vessel ratio stent 100 is constrained to a reduced or expanded length, e.g., by longitudinally compressing or expanding high metal to vessel ratio stent 100. When in the constrained configuration, either in length, diameter, or both, holes 110 are collapsed resulting in a much higher metal to vessel ratio for high metal to vessel ratio stent 100 than when high metal to vessel ratio stent 100 and is in its final configuration.

As discussed further below, e.g., in reference to FIGS. 14-17, the metal to vessel ratio of high metal to vessel ratio stent 100 is sufficiently high to encourage tissue ingrowth around high metal to vessel ratio stent 100. However, the metal to vessel ratio of high metal to vessel ratio stent 100 is sufficiently low to ensure adequate perfusion of branch vessel(s) through high metal to vessel ratio stent 100.

Generally, the metal to vessel ratio of high metal to vessel ratio stent 100 is within the range of 30 percent to 80 percent (30-80%), more suitably within the range of 35 percent to 60 percent (35-60%). In one particular embodiment, the metal to vessel ratio is 40 percent (40%).

In one embodiment, high metal to vessel ratio stent 100 is formed of balloon expandable and/or self-expanding metal, e.g., e.g., formed of Nitinol or stainless steel. In one embodiment, high metal to vessel ratio stent 100 is a laser cut, etched, or wire formed stent. For example, a cylindrical tube of metal, e.g., Nitinol, is cut with a laser and/or by etching to form holes 110 therein thus forming high metal to vessel ratio stent 100. The cylindrical tube of metal can be formed from a metal sheet that is bent and welded in one embodiment.

As illustrated in FIG. 2, high metal to vessel ratio stent 100 has a thickness T, e.g., equal to the thickness of the cylindrical tube from which high metal to vessel ratio stent 100 is formed. Thickness T is the distance between the inner cylindrical surface 118 and the outer cylindrical surface 120 of high metal to vessel ratio stent 100.

Figure 3:
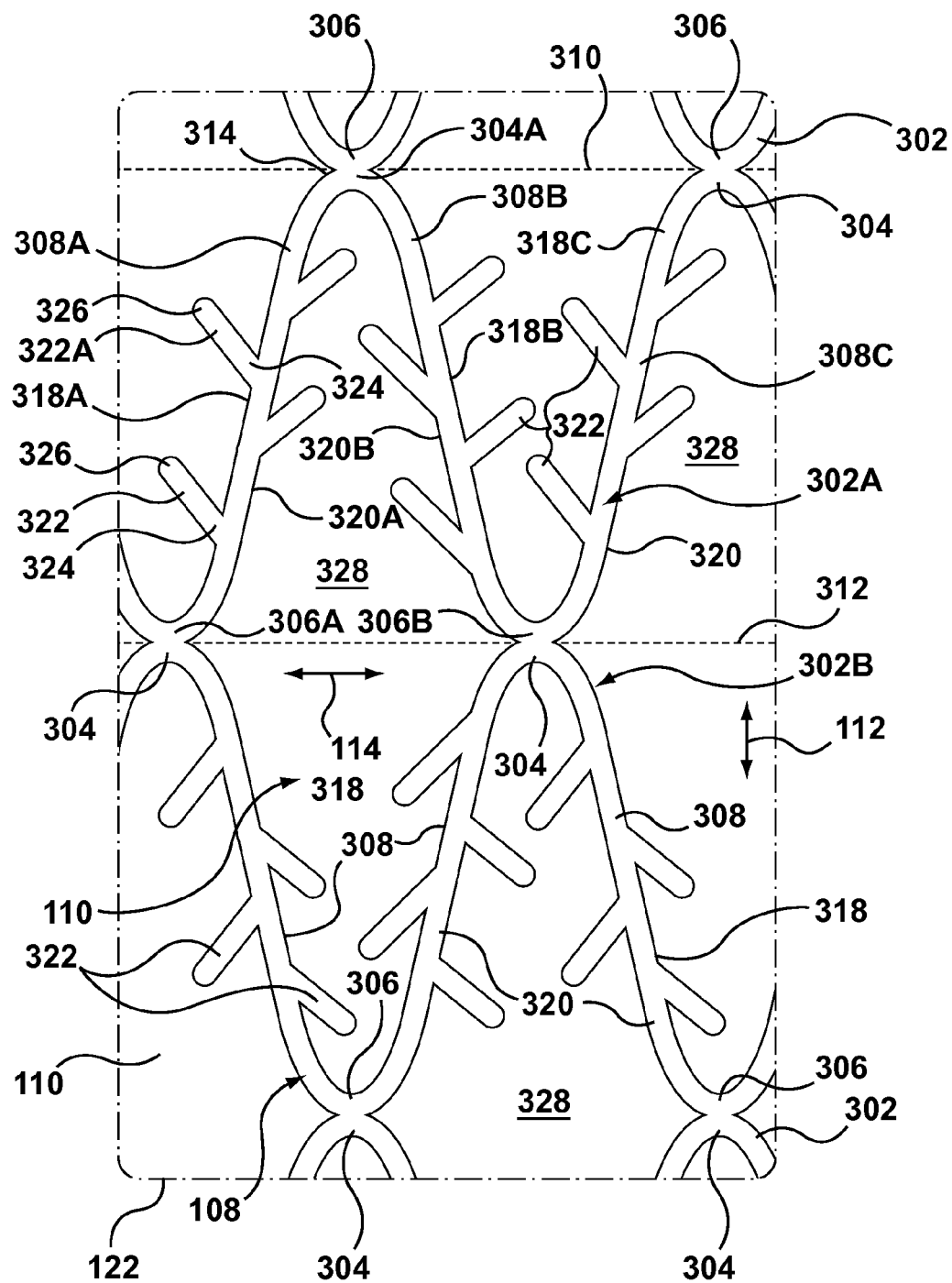
FIG. 3 is an enlarged plan view of a region of the high metal to vessel ratio stent of FIG. 1 in its final configuration in accordance with one embodiment.

FIG. 3 is an enlarged plan view of the region 122 of high metal to vessel ratio stent 100 of FIG. 1 in its final configuration in accordance with one embodiment. Referring now to FIG. 3, high metal to vessel ratio stent 100 includes a plurality of serpentine rings 302 connected together.

Serpentine rings 302 includes a zigzag pattern, sometimes called a sinusoidal or an alternating repeating pattern. More particularly, each serpentine ring 302 includes a repeating pattern of proximal apexes 304 and distal apexes 306 connected by struts 308. Proximal apexes 304 and distal apexes 306 are sometimes called peaks and valleys, respectively, or crowns.

Proximal apexes 304 define the proximal edge 310 of each serpentine ring 302. Proximal edge 310 is an imaginary circle at proximal apexes 304 in a plane perpendicular to longitudinal axis L of high metal to vessel ratio stent 100.

Similarly, distal apexes 306 define the distal edge 312 of each serpentine ring 302. Distal edge 312 is an imaginary circle at distal apexes 306 in a plane perpendicular to longitudinal axis L of high metal to vessel ratio stent 100. Struts 308 generally extend between proximal edge 310 and distal edge 312 of each serpentine ring 302.

To illustrate, serpentine rings 302 include a first serpentine ring 302A. Serpentine ring 302A includes a proximal edge 310 at proximal apexes 304, a distal edge 312 at distal apexes 306, and struts 308 extending between proximal edge 310 and distal edge 312.

To further illustrate, serpentine ring 302A includes a first distal apex 306A and a second distal apex 306B of the plurality of distal apexes 306 of serpentine ring 302A. Serpentine ring 302A includes a first proximal apex 304A of the plurality of proximal apexes 304 of serpentine ring 302A. Serpentine ring 302A further includes a first strut 308A and a second strut 308B of the plurality of struts 308 of serpentine ring 302A. Distal apex 306A is connected to proximal apex 304A by strut 308A. Proximal apex 304A is connected to distal apex 306B by strut 308B.

Each proximal apex 304 has two respective struts 308 extending therefrom. To illustrate, proximal apex 304A has struts 308A, 308B extending therefrom, which are thus the two respective struts 308 of proximal apex 304A.

Each proximal apex 304 includes an extrados surface 314 and an intrados surface 316. Extrados surface 314 is the exterior surface of the curve of each proximal apex 304. In contrast, intrados surface 316 is the interior surface of the curve of a proximal apex 304.

Further, with respect to proximal apexes 304, each strut 308 includes an exterior radial surface 318 and an interior radial surface 320. Exterior radial surfaces 318 are further outward, or exterior, to interior radial surfaces 320 in circumferential direct 114 with respect to the respective proximal apex 304. Exterior radial surfaces 318 and interior radial surfaces 320 are parallel to and extend in radial direction 116 from inner cylindrical surface 118 to outer cylindrical surface 120 of high metal to vessel ratio stent 100.

Generally, exterior radial surfaces 318 are continuous with extrados surfaces 314 and interior radial surfaces 320 are continuous with intrados surfaces 316.

To illustrate, with respect to proximal apex 304A, strut 308A includes an exterior radial surface 318A and an interior radial surface 320A. Further, with respect to proximal apex 304A, strut 308B includes an exterior radial surface 318B and an interior radial surface 320B.

Proximal apexes 304 of serpentine rings 302 are directly connected to distal apexes 306 of the adjacent proximal serpentine ring 302. To illustrate, serpentine rings 302 include a second serpentine ring 302B. Proximal apexes 304 of serpentine ring 302B are connected to distal apexes 306 of serpentine ring 302A. Note serpentine ring 302A is proximal to serpentine ring 302B.

Of course, the proximal apexes 304 of the most proximal of serpentine rings 302 are unconnected to another serpentine ring and define the proximal end 100P of high metal to vessel ratio stent 100. Similarly, the distal apexes 306 of the most distal of serpentine rings 302 are unconnected to another serpentine ring and define the distal end 100D of high metal to vessel ratio stent 100.

To increase the metal to vessel ratio of high metal to vessel ratio stent 100, each strut 308 includes a plurality of fingers 322. Fingers 322 increase the surface area of material 108 as compared to the area of serpentine rings 302 alone.

Fingers 322 are protrusions that protrude from struts 308 in a direction along the imaginary cylinder of high metal to vessel ratio stent 100. More particularly, each finger 322 includes a knuckle 324 directly attached to a strut 308 and a tip 326. Each finger 322 extends from knuckle 324 and strut 308 to tip 326, where the finger 322 ends.

To illustrate, a first finger 322A of the plurality of fingers 322 is attached to strut 308A. Finger 322A includes a knuckle 324 directly attached to strut 308A and a tip 326.

In accordance with this embodiment, each strut 308 includes a plurality of fingers 322 on both the exterior radial surface 318 and the interior radial surface 320. To illustrate, strut 308A includes fingers 322 on exterior radial surface 318A and interior radial surface 320A.

In accordance with this embodiment, with respect to a proximal apex 304, the pattern of fingers 322 on an interior radial surface 320 of a first strut 308 of the two respective struts 308 of the proximal apex 304 is the same, or approximately the same, as the pattern of fingers 322 on an exterior radial surface 318 of a second strut 308 of the two respective struts 308 of the proximal apex 304.

To illustrate, with respect to proximal apex 304A, the pattern of fingers 322 on interior radial surface 320A (or 320B) of a first strut 308A (or 308B) of the two respective struts 308A, 308B of proximal apex 304A is the same as the pattern of fingers 322 on exterior radial surface 318B (or 318A) of a second strut 308B of the two respective struts 308A, 308B of proximal apex 304A, respectively.

With respect to a proximal apex 304, the pattern of fingers 322 on an interior radial surface 320 of a first strut 308 of the two respective struts 308 of the proximal apex 304 is different than, and interdigitated with, the pattern of fingers 322 on an interior radial surface 320 of a second strut 308 of the two respective struts 308 of the proximal apex 304.

To illustrate, with respect to proximal apex 304A, the pattern of fingers 322 on interior radial surface 320A of a first strut 308A of the two respective struts 308A, 308B of proximal apex 304A is different than, and interdigitated with, the pattern of fingers 322 on interior radial surface 320B of a second strut 308B of the two respective struts 308A, 308B of proximal apex 304A, respectively.

Generally, fingers 322 on directly adjacent radial surfaces of directly adjacent struts 308 are interdigitated with one another. To illustrate, fingers 322 on exterior radial surface 318B of strut 308B are interdigitated with fingers 322 on a directly adjacent exterior radial surface 318C of the directly adjacent strut 308C.

By having fingers 322 on directly adjacent radial surfaces of directly adjacent struts 308 be interdigitated, e.g., interlocked like the fingers of folded hands when in the constrained configuration, high metal to vessel ratio stent 100 can be radially collapsed to an extremely small diameter.

As discussed above, high metal to vessel ratio stent 100 includes a plurality of holes 110. In accordance with this embodiment, each hole 110 is defined by a stent cell 328 of high metal to vessel ratio stent 100.

More particularly, stent cell 328 is defined by: (1) a proximal apex 304 of a first serpentine ring 302; (2) the respective struts 308 of element (1); (3) the respective distal apexes 306 connected to element (2); (4) the proximal apexes 304 of the next serpentine ring 302 that are connected to element (3); (5) the directly adjacent struts 308 that are connected to element (4); (6) the distal apex 306 connected to element (5), and the fingers 322 protruding into the respective hole 110 from elements (2), (5).

Figure 4:
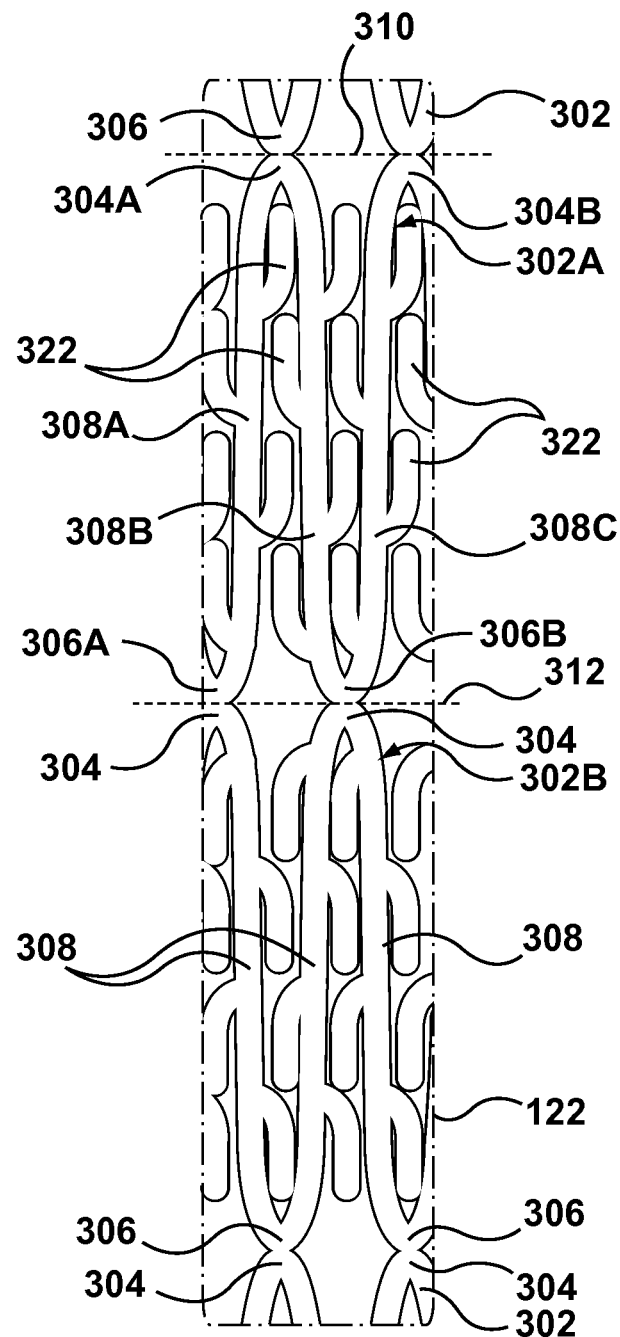
FIG. 4 is an enlarged plan view of the region of the high metal to vessel ratio stent of FIG. 3 in its constrained configuration in accordance with one embodiment.

FIG. 4 is an enlarged plan view of the region 122 of high metal to vessel ratio stent 100 of FIG. 3 in its constrained configuration in accordance with one embodiment. FIG. 4 corresponds to the view of FIG. 3, however, in FIG. 4, high metal to vessel ratio stent 100 is in the constrained, e.g., radially collapsed, configuration, whereas in FIG. 3, high metal to vessel ratio stent 100 is in the final, e.g., radially expanded, configuration.

As illustrated in FIG. 4, when in the constrained configuration, fingers 322 on directly adjacent radial surfaces of directly adjacent struts 308 fit one within another, i.e., are interdigitated. This allows high metal to vessel ratio stent 100 to be radially collapsed to an extremely small diameter.

Figure 5:
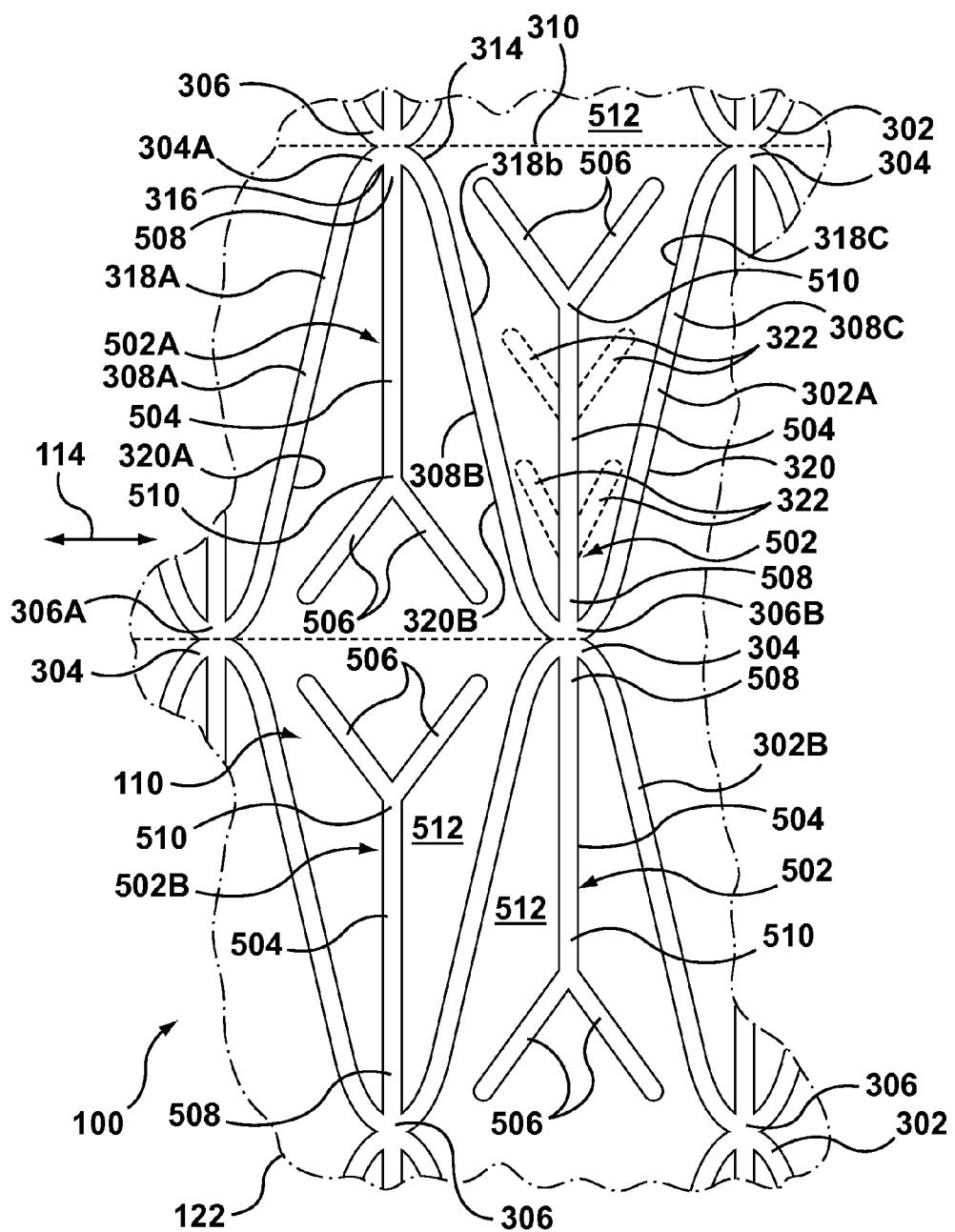
FIG. 5 is an enlarged plan view of the region of the high metal to vessel ratio stent of FIG. 1 in its final configuration in accordance with another embodiment.

FIG. 5 is an enlarged plan view of the region 122 of high metal to vessel ratio stent 100 of FIG. 1 in its final configuration in accordance with another embodiment. Region 122 as illustrated in FIG. 5 is similar to region 122 as illustrated in FIG. 3 and only the significant differences are discussed below.

Referring now to FIG. 5, high metal to vessel ratio stent 100 includes serpentine rings 302 including serpentine rings 302A, 302B, proximal apexes including proximal apex 304A, distal apexes 306 including distal apexes 306A, 306B, struts 308 including struts 308A, 308B, 308C, proximal edges 310, distal edges 312, extrados surfaces 314, intrados surfaces 316, exterior radial surfaces 318 including exterior radial surfaces 318A, 318B, 318C, internal radial surfaces 320 including internal radial surfaces 320A, 320B as discussed above in relation to FIGS. 3, 4.

In accordance with this embodiment, to increase the metal to vessel ratio of high metal to vessel ratio stent 100, high metal to vessel ratio stent 100 includes projections 502. More particularly, a projection 502 is attached to each proximal apex 304 and protrudes distally therefrom. Similarly, a projection 502 is attached to each distal apex 306 and protrudes proximal therefrom.

Projections 502 including stems 504 and petals 506. Stems 504 include serpentine ring attachment ends 508 and petal attachment ends 510. Serpentine ring attachment ends 508 are directly attached to a serpentine ring 302, i.e., a proximal apex 304 or a distal apex 306. Petals 506 are directly attached to petal attachment ends 510 of stems 504.

In accordance with this embodiment, each projection 502 includes two petals 506. Petals 506 are located in circumferential direction 114 approximately between directly adjacent apexes of a serpentine ring 302.

To illustrate, a first projection 502A is attached to proximal apex 304A of serpentine ring 302A and protrudes distally therefrom. Similarly, a second projection 502B is attached to a distal apex 306 of serpentine ring 302B and protrudes proximal therefrom.

To further illustrate, petals 506 of first projection 502A are located in circumferential direction 114 between directly adjacent distal apexes 306A, 306B of serpentine ring 302A. To further illustrate, petals 506 of second projection 502B are located in circumferential direction 114 between directly adjacent proximal apexes 304 of serpentine ring 302B.

As illustrated by dashed lines on the projection 502 at the upper right of FIG. 5, in one embodiment, to further increase the metal to vessel ratio of high metal to vessel ratio stent 100, each stem 504 includes a plurality of fingers 322 attached thereto. Fingers 322, and the number thereof, are optional, and generally are provided to obtain a desired metal to vessel ratio of high metal to vessel ratio stent 100.

As discussed above, high metal to vessel ratio stent 100 includes a plurality of holes 110. In accordance with this embodiment, each hole 110 is defined by a stent cell 512 of high metal to vessel ratio stent 100.

More particularly, stent cell 512 is defined by: (1) a proximal apex 304 of a first serpentine ring 302; (2) the respective struts 308 of element (1); (3) the respective distal apexes 306 connected to element (2); (4) the proximal apexes 304 of the next serpentine ring 302 that are connected to element (3); (5) the directly adjacent struts 308 that are connected to element (4); (6) the distal apex 306 connected to element (5), and the projections 502 protruding into the respective hole 110 from elements (1), (6).

Stems 504 extend longitudinally between adjacent struts 308 where the spacing between struts 308 is relatively small. In contrast, petals 506 are located between adjacent struts 308 where the spacing between struts 308 is relatively large. This allows high metal to vessel ratio stent 100 to be radially collapsed to an extremely small diameter as illustrated in FIG. 6.

Figure 6:
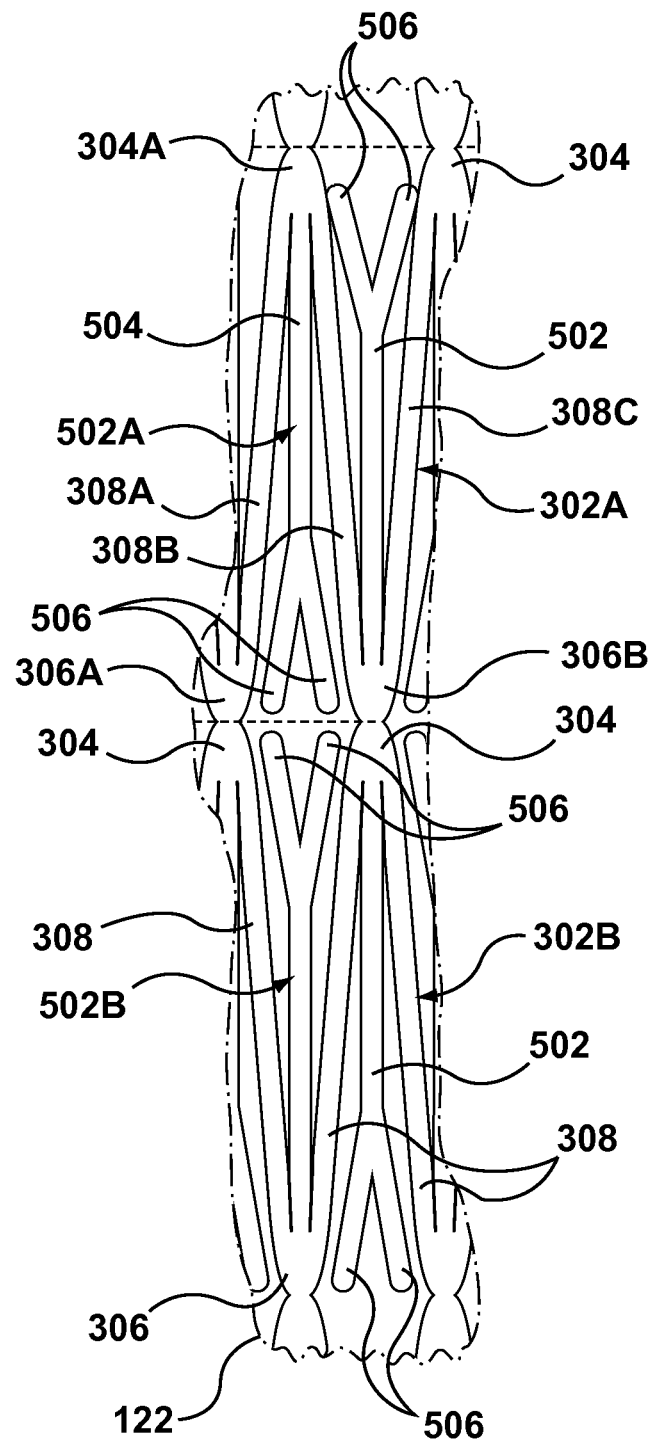
FIG. 6 is an enlarged plan view of the region of the high metal to vessel ratio stent of FIG. 5 in its constrained configuration in accordance with one embodiment.

FIG. 6 is an enlarged plan view of the region 122 of high metal to vessel ratio stent 100 of FIG. 5 in its constrained configuration in accordance with one embodiment. FIG. 6 corresponds to the view of FIG. 5, however, in FIG. 6, high metal to vessel ratio stent 100 is in the constrained, e.g., radially collapsed, configuration, whereas in FIG. 5, high metal to vessel ratio stent 100 is in the final, e.g., radially expanded, configuration.

As illustrated in FIG. 6, when in the constrained configuration, projections 502 are collapsed between adjacent struts 308. This allows high metal to vessel ratio stent 100 to be radially collapsed to an extremely small diameter.

Figure 7:
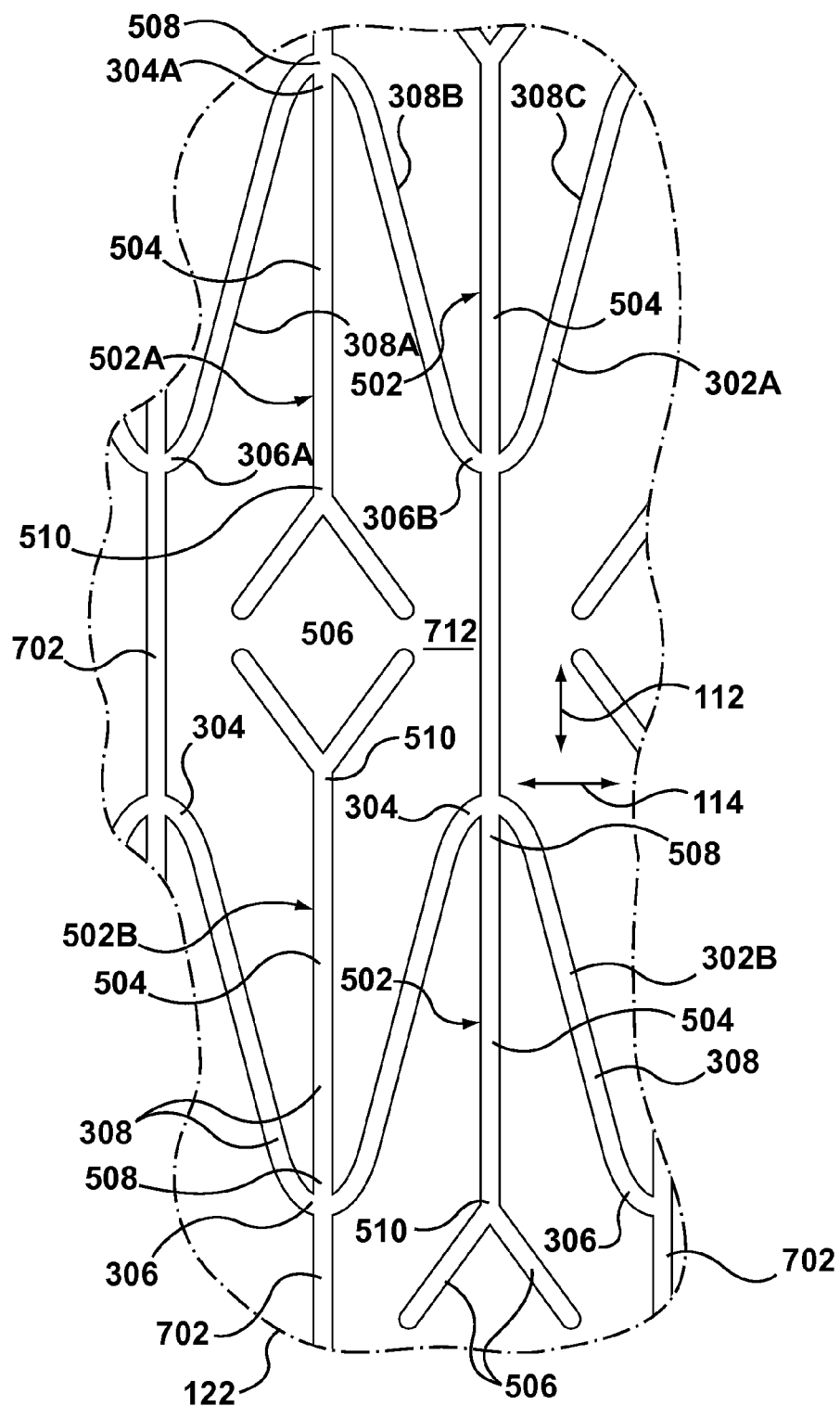
FIG. 7 is an enlarged plan view of the region of the high metal to vessel ratio stent of FIG. 1 in its final configuration in accordance with yet another embodiment.

FIG. 7 is an enlarged plan view of the region 122 of high metal to vessel ratio stent 100 of FIG. 1 in its final configuration in accordance with yet another embodiment. Region 122 as illustrated in FIG. 7 is similar to region 122 as illustrated in FIG. 5 and only the significant differences are discussed below.

Referring now to FIG. 7, high metal to vessel ratio stent 100 includes serpentine rings 302 including serpentine rings 302A, 302B, proximal apexes including proximal apex 304A, distal apexes 306 including distal apexes 306A, 306B, struts 308 including struts 308A, 308B, 308C, projections 502 including projections 502A, 502B, stems 504 and petals 506.

In accordance with this embodiment, to further increase the ability to radially collapse high metal to vessel ratio stent 100, high metal to vessel ratio stent 100 includes serpentine ring connectors 702. More particularly, proximal apexes 304 of serpentine rings 302 are connected to distal apexes 306 of the adjacent proximal serpentine ring 302 by serpentine ring connectors 702. Serpentine ring connectors 702 are straight segments extending in longitudinal direction 112 in accordance with this embodiment.

As discussed above, high metal to vessel ratio stent 100 includes a plurality of holes 110. In accordance with this embodiment, each hole 110 is defined by a stent cell 712 of high metal to vessel ratio stent 100.

More particularly, stent cell 712 is defined by: (1) a proximal apex 304 of a first serpentine ring 302; (2) the respective struts 308 of element (1); (3) the respective distal apexes 306 connected to element (2); (4) the serpentine ring connectors 702 connected to element (3); (5) the proximal apexes 304 of the next serpentine ring 302 that are connected to element (4); (6) the directly adjacent struts 308 that are connected to element (5); (7) the distal apex 306 connected to element (6), and the projections 502 protruding into the respective hole 110 from elements (1), (7).

Serpentine ring connectors 702 space adjacent serpentine rings 302 from each other in longitudinal direction 112. In accordance with this embodiment, stems 504 of projections 502 extend longitudinally into this space between adjacent serpentine rings 302. Accordingly, petals 506 of projections 502 are located in circumferential direction 114 between directly adjacent serpentine ring connectors 702.

Figure 8:
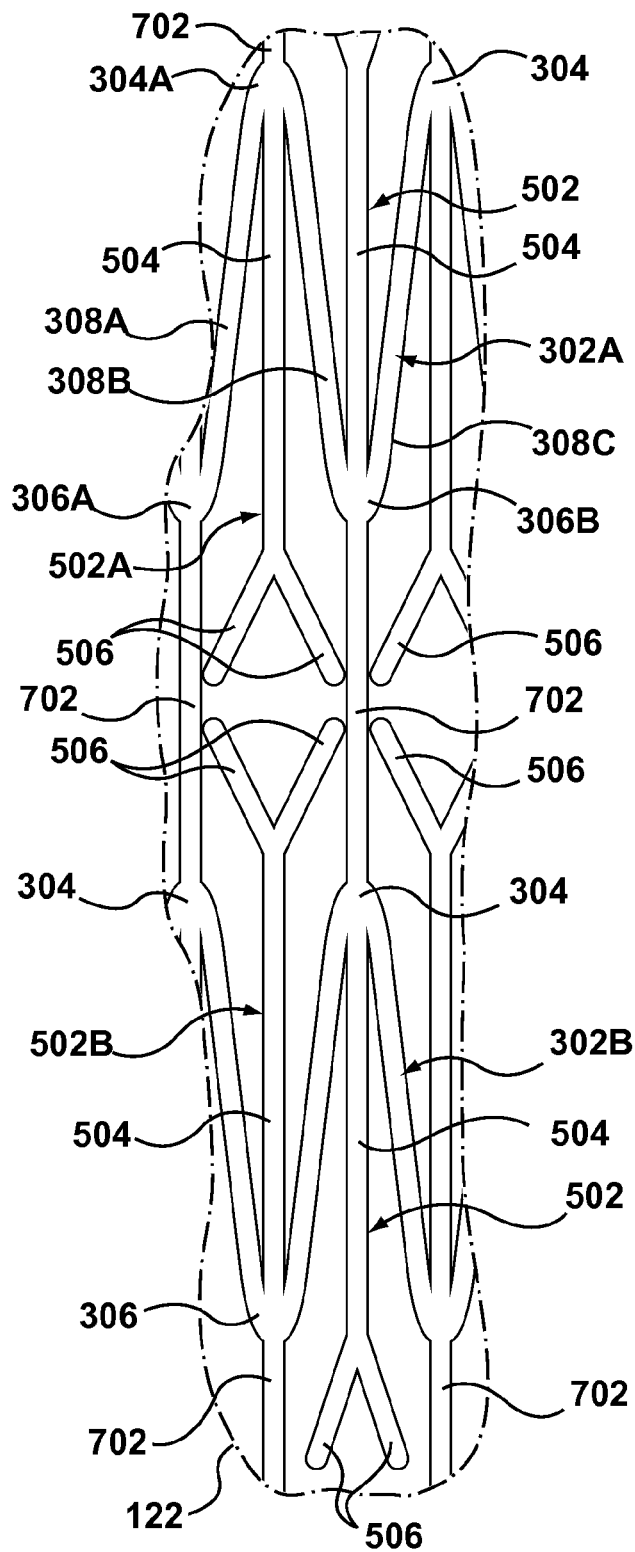
FIG. 8 is an enlarged plan view of the region of the high metal to vessel ratio stent of FIG. 7 in its constrained configuration in accordance with one embodiment.

By using serpentine ring connectors 702 to space apart serpentine rings 302 and placing petals 506 within this space, high metal to vessel ratio stent 100 can be radially collapsed to an extremely small diameter as illustrated in FIG. 8.

FIG. 8 is an enlarged plan view of the region 122 of high metal to vessel ratio stent 100 of FIG. 7 in its constrained configuration in accordance with one embodiment. FIG. 8 corresponds to the view of FIG. 7, however, in FIG. 8, high metal to vessel ratio stent 100 is in the constrained, e.g., radially collapsed, configuration, whereas in FIG. 7, high metal to vessel ratio stent 100 is in the final, e.g., radially expanded, configuration.

As illustrated in FIG. 8, when in the constrained configuration, petals 506 are collapsed between serpentine ring connectors 702. This allows high metal to vessel ratio stent 100 to be radially collapsed to an extremely small diameter.

Figure 9:
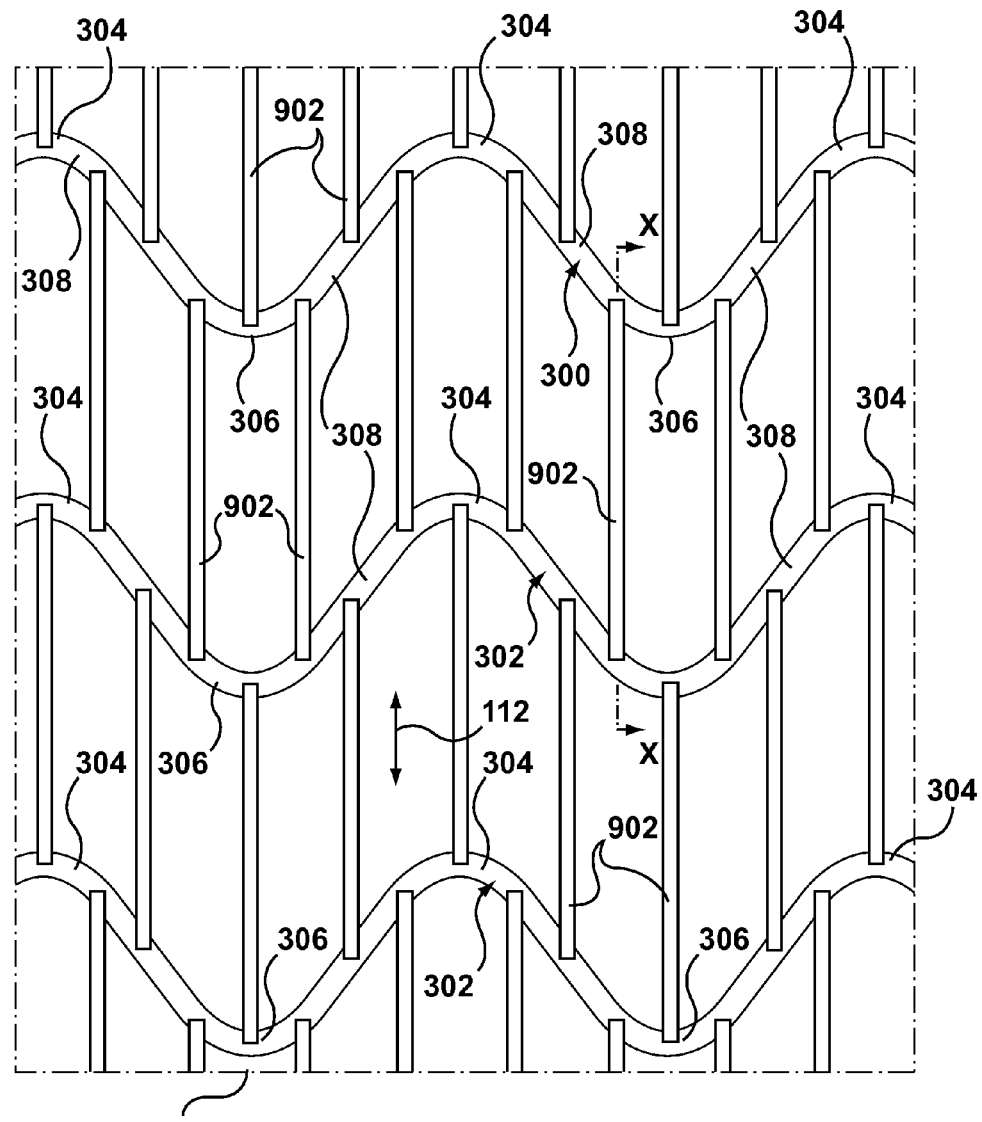
FIG. 9 is an enlarged plan view of the region of the high metal to vessel ratio stent of FIG. 1 in its final configuration in accordance with yet another embodiment.

FIG. 9 is an enlarged plan view of the region 122 of high metal to vessel ratio stent 100 of FIG. 1 in its final configuration in accordance with yet another embodiment. Region 122 as illustrated in FIG. 9 is similar to region 122 as illustrated in FIG. 3 and only the significant differences are discussed below.

Referring now to FIG. 9, high metal to vessel ratio stent 100 includes serpentine rings 302, proximal apexes 304, distal apexes 306, and struts 308.

In accordance with this embodiment, to increase the metal to vessel ratio of high metal to vessel ratio stent 100, high metal to vessel ratio stent 100 includes serpentine ring connectors 902. More particularly, serpentine rings 302 are connected to one another by serpentine ring connectors 902.

Serpentine ring connectors 902 are straight segments, e.g., thin flexible beams, extending in longitudinal direction 112 in accordance with this embodiment. However, in other embodiments, serpentine ring connectors 902 are angled, curved, or otherwise nonlinear connectors and can be oriented in any direction, e.g., longitudinally, diagonally, crossing, or other direction. Further, serpentine ring connectors 902 can be attached to serpentine rings 302 at proximal apexes 304, distal apexes 306, and to struts 308.

By providing a particular number of serpentine ring connectors 902, a desired metal to vessel ratio of high metal to vessel ratio stent 100 is obtained.

Figure 10:
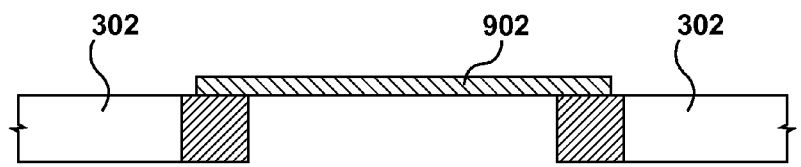
FIG. 10 is a cross-section view of the high metal to vessel ratio stent along the line X-X of FIG. 9 in accordance with one embodiment.

FIG. 10 is a cross-section view of high metal to vessel ratio stent 100 along the line X-X of FIG. 9 in accordance with one embodiment. As illustrated in FIG. 10, in accordance with this embodiment, serpentine ring connectors 902 are physically attached, e.g., by welding, to serpentine rings 302. Further, the thickness of serpentine rings 302 is greater than the thickness of serpentine ring connectors 902.

Figure 11:
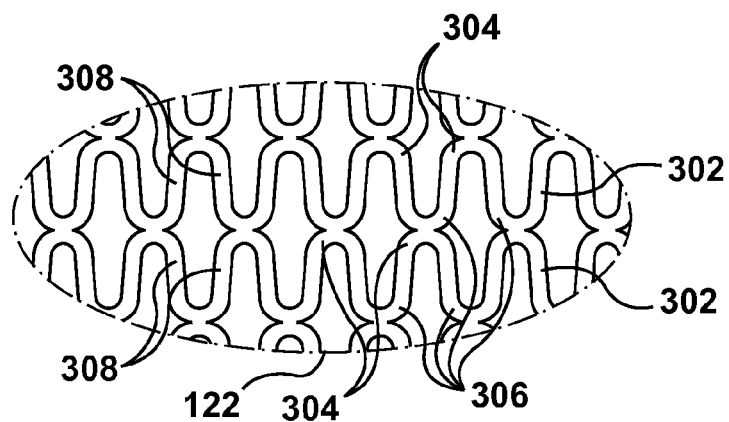
FIG. 11 is an enlarged plan view of the region of the high metal to vessel ratio stent of FIG. 1 in its final configuration in accordance with yet another embodiment.

FIG. 11 is an enlarged plan view of the region 122 of high metal to vessel ratio stent 100 of FIG. 1 in its final configuration in accordance with yet another embodiment. Region 122 as illustrated in FIG. 11 is similar to region 122 as illustrated in FIG. 3 and only the significant differences are discussed below.

Referring now to FIG. 11, high metal to vessel ratio stent 100 includes serpentine rings 302, proximal apexes 304, distal apexes 306, and struts 308.

In accordance with this embodiment, to increase the metal to vessel ratio of high metal to vessel ratio stent 100, high metal to vessel ratio stent 100 includes a high number of serpentine rings 302 with short lengths. More particularly, each serpentine ring 302 includes 20-30 proximal apexes 304 and correspondingly, 20-30 distal apexes 306.

Figure 12:
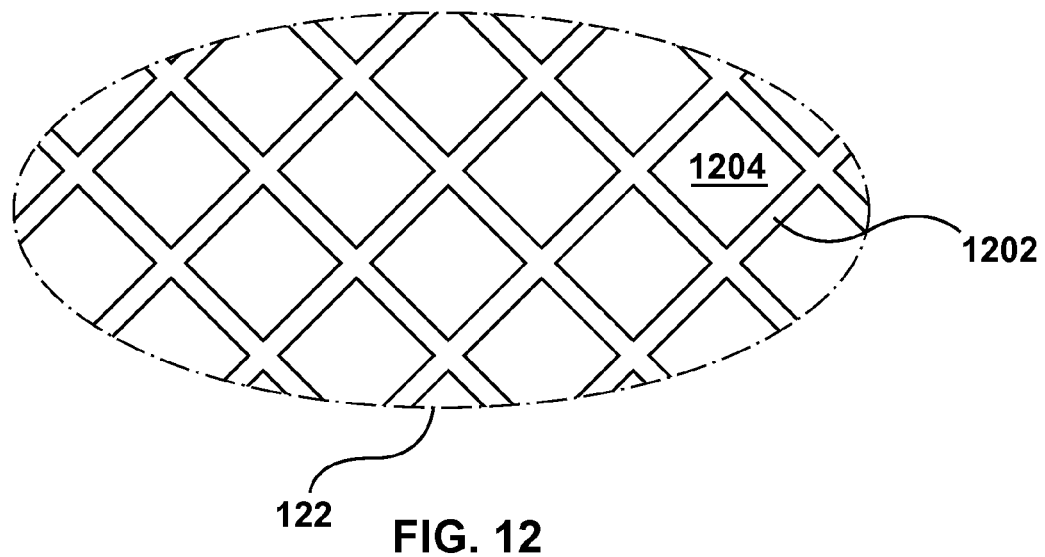
FIG. 12 is an enlarged plan view of the region of the high metal to vessel ratio stent of FIG. 1 in its final configuration in accordance with yet another embodiment.

FIG. 12 is an enlarged plan view of the region 122 of high metal to vessel ratio stent 100 of FIG. 1 in its final configuration in accordance with yet another embodiment. Referring now to FIG. 12, high metal to vessel ratio stent 100 includes diamond rings 1202 connected together. Diamond rings 1202 define stent cells 1204. By providing a plurality of stent cells 1204, a high metal to vessel ratio is achieved.

Further, serpentine rings 302 as illustrated in FIG. 11 can be combined with diamond rings 1202 as illustrated in FIG. 12 to form high metal to vessel ratio stent 100 in accordance with other embodiments. The amplitude of the serpentine rings 302 and/or diamond rings 1202 can be varied.

Figure 13:
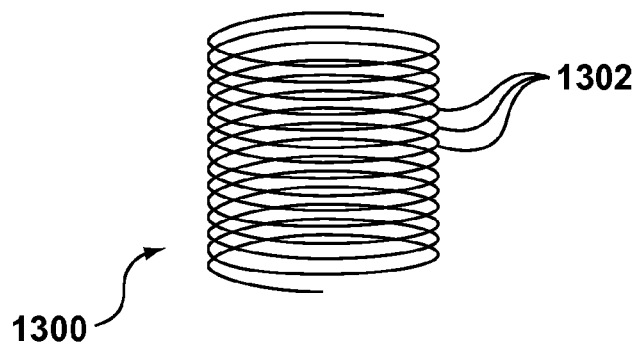
FIG. 13 is a perspective view of a high metal to vessel ratio stent in accordance with another embodiment.

FIG. 13 is a perspective view of a high metal to vessel ratio stent 1300 in accordance with another embodiment. Referring now to FIG. 13, high metal to vessel ratio stent 1300 is a coil stent, i.e., a coil of material.

High metal to vessel ratio stent 1300 includes a plurality of windings 1302. In accordance with this embodiment, by controlling how close the windings 1302 are, i.e., by longitudinally packing or stretching high metal to vessel ratio stent 1300, the metal to vessel ratio of high metal to vessel ratio stent 1300 can be controlled. Although delivery of high metal to vessel ratio stent 100 of FIGS. 1 and 2 is discussed below in reference to FIGS. 14-18, the discussion is equally applicable to delivery of high metal to vessel ratio stent 1300 of FIG. 13.

Figure 14:
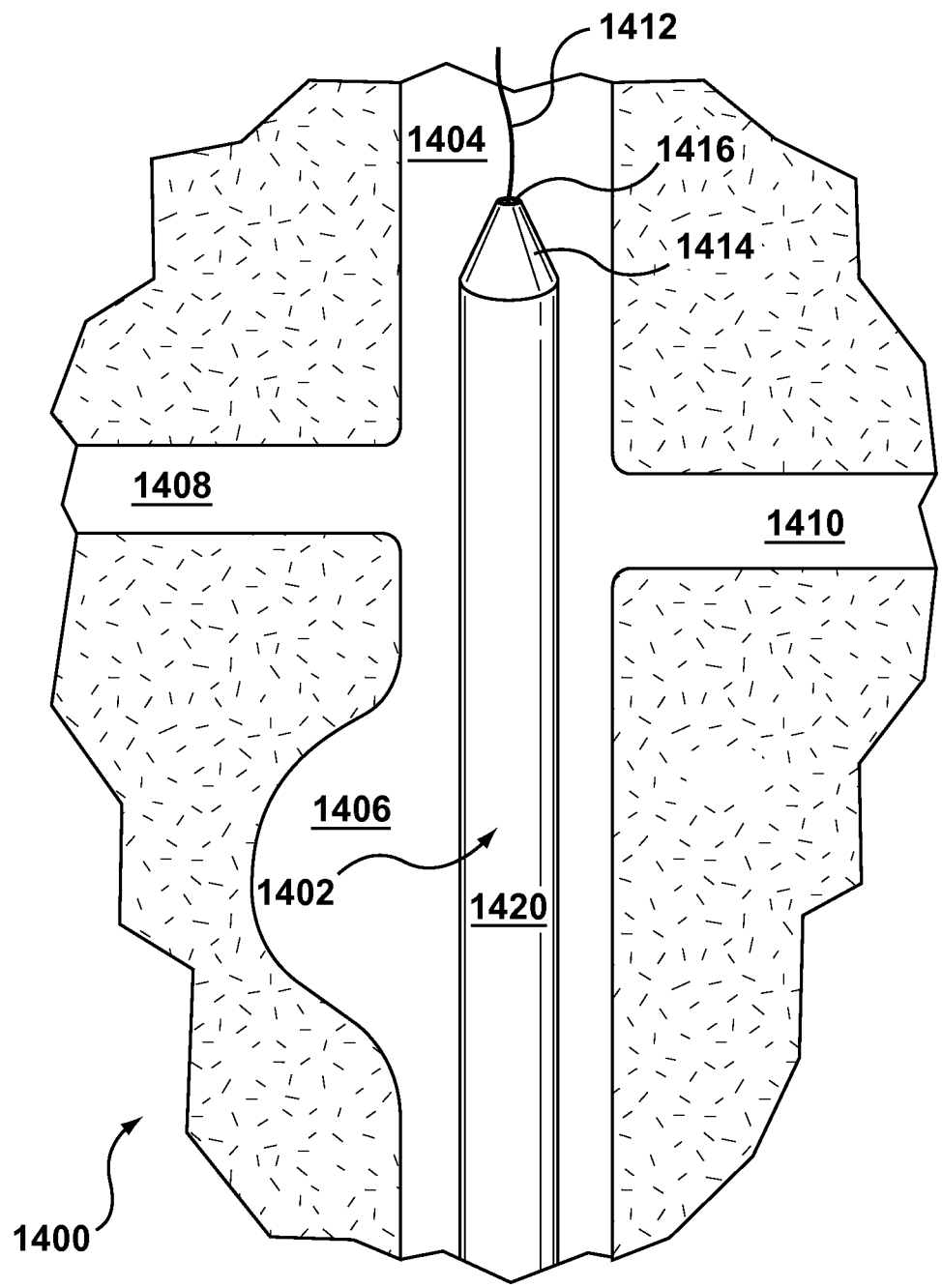
FIG. 14 is a cross-sectional view of a vessel assembly including a delivery system including the high metal to vessel ratio stent of FIGS. 1 and 2 in accordance with one embodiment.
Figure 15:
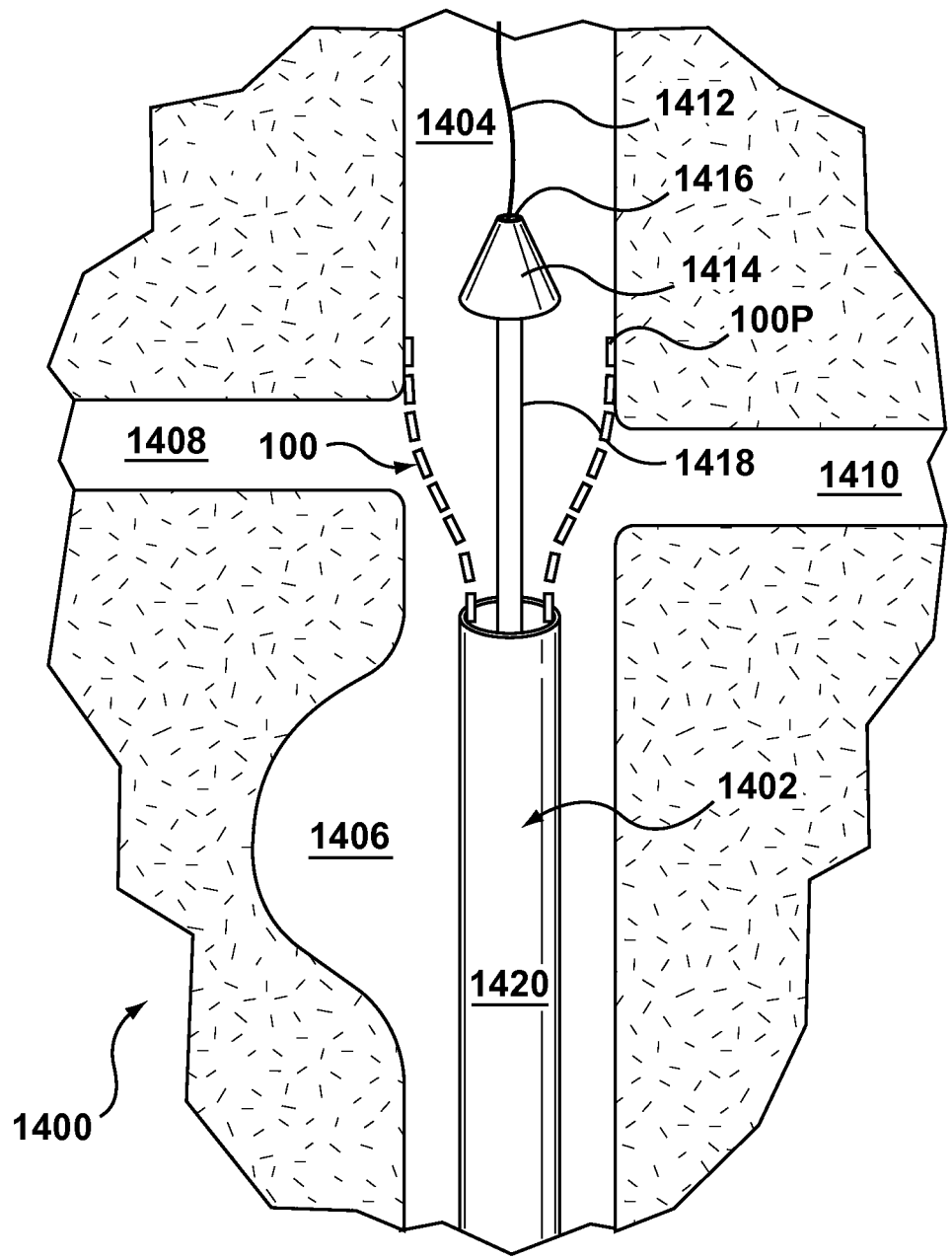
FIG. 15 is a cross-sectional view of the vessel assembly including the delivery system at a later stage of deploying the high metal to vessel ratio stent of FIGS. 1 and 2 in accordance with one embodiment.

FIG. 14 is a cross-sectional view of a vessel assembly 1400 including a delivery system 1402 including high metal to vessel ratio stent 100 of FIGS. 1 and 2 in accordance with one embodiment. FIG. 15 is a cross-sectional view of vessel assembly 1400 including delivery system 1402 at a later stage of deploying high metal to vessel ratio stent 100 of FIGS. 1 and 2 in accordance with one embodiment.

Referring now to FIGS. 14 and 15 together, a main vessel 1404, e.g., the aorta, includes an aneurysm 1406. High metal to vessel ratio stent 100, sometimes called a prosthesis, is deployed into main vessel 1404 to exclude aneurysm 1406 using delivery system 1402.

Emanating from main vessel 1404 is a first branch vessel 1408 and a second branch vessel 1410, sometimes called visceral branches of the abdominal aorta. The location of branch vessels 1408, 1410 vary from patient to patient. Examples of branch vessels 1408, 1410 include the renal arteries (RA), the superior mesenteric artery (SMA), the brachiocephalic artery, the left subclavian artery, the left common carotid, the celiac trunk, and the hypogastric artery.

Delivery system 1402 is advanced to the location of aneurysm 1406, e.g., over a guidewire 1412, for example as illustrated in FIG. 14. Delivery system 1402 includes a tapered tip 1414 that is flexible and able to provide trackability in tight and tortuous vessels. Tapered tip 1414 includes a lumen 1416 allowing for passage of guidewire 1412 in accordance with this embodiment. In one embodiment, delivery system 1402 includes radiopaque marker(s) that allow visualization of delivery system 1402.

To deploy high metal to vessel ratio stent 100, an inner member 1418 of delivery system 1402 including tapered tip 1414 mounted thereon is held stationary while an outer sheath 1420 of delivery system 1402 is withdrawn, for example, as illustrated in FIG. 15. High metal to vessel ratio stent 100 is radially constrained by outer sheath 1420 around inner member 1418. Inner member 1418 includes a stent stop or other features to prevent high metal to vessel ratio stent 100 from moving back as outer sheath 1420 is withdrawn.

As outer sheath 1420 is withdrawn, high metal to vessel ratio stent 100 is gradually exposed from proximal end 100P to distal end 100D of high metal to vessel ratio stent 100. The exposed portion of high metal to vessel ratio stent 100 radially expands to be in conforming surface contact with main vessel 1404. More particularly, high metal to vessel ratio stent 100 opposes the walls of main vessel 1404 thus securing high metal to vessel ratio stent 100 in place.

In one embodiment, high metal to vessel ratio stent 100 is self-expanding and thus self expands upon being released from outer sheath 1420. However, in other embodiments, high metal to vessel ratio stent 100 is expanded with a balloon or other expansion device.

Although a particular delivery system 1402 is illustrated in FIGS. 14, 15 and discussed above, in light of this disclosure, those of skill in the art will understand that any one of a number of delivery systems can be used to deploy high metal to vessel ratio stent 100 and the particular delivery system used is not essential to this embodiment.

FIG. 16 is a cross-sectional view of vessel assembly 1400 of FIGS. 14-15 after deployment of high metal to vessel ratio stent 100 of FIGS. 1 and 2 in accordance with one embodiment. Referring now to FIG. 16, high metal to vessel ratio stent 100 is in conforming surface contact with main vessel 1404. High metal to vessel ratio stent 100 is deployed such that high metal to vessel ratio stent 100 covers, sometimes called jails, ostai (plural of ostium) 1422, 1424 of branch vessels 1408, 1410, respectively.

However, as high metal to vessel ratio stent 100 is permeable, blood flows from main vessel 1404 through high metal to vessel ratio stent 100 and into branch vessels 1408, 1410 thus perfusing branch vessels 1408, 1410. In one embodiment, branch vessels 1408, 1410 are continuously perfused during the entire procedure of deploying high metal to vessel ratio stent 100.

Further, deployment of high metal to vessel ratio stent 100 is relatively simple thus minimizing the complexity and thus risk of deploying high metal to vessel ratio stent 100. More particularly, as the entire high metal to vessel ratio stent 100 is permeably, high metal to vessel ratio stent 100 is deployed without having to rotationally position high metal to vessel ratio stent 100 to be aligned with branch vessels 1408, 1410.

Further, high metal to vessel ratio stent 100 is deployed with fixation and sealing to main vessel 1404 superior to aneurysm 1406, e.g., to healthy tissue of main vessel 1404 adjacent branch vessels 1408, 1410. This minimizes the risk of migration of high metal to vessel ratio stent 100. Further, this allows fixation and sealing of high metal to vessel ratio stent 100 to healthy tissue even when aneurysm 1406 has a short neck, i.e., when the distance between aneurysm 1406 and branch vessels 1408, 1410 is relatively small, as well as when aneurysm 1406 has a highly angulated neck.

Further, high metal to vessel ratio stent 100 covers and excludes aneurysm 1406. More particularly, once high metal to vessel ratio stent 100 is anchored within main vessel 1404, blood flows through main lumen 106 thus excluding aneurysm 1406.

Further, high metal to vessel ratio stent 100 is deployed with fixation and sealing to main vessel 1404 inferior to aneurysm 1406, e.g., to healthy tissue of main vessel 1404. This further facilitates exclusion of aneurysm 1406 while at the same time minimizes the risk of migration of high metal to vessel ratio stent 100.

In other examples, high metal to vessel ratio stent 100 is a bifurcated stent, e.g., high metal to vessel ratio stent 100 is bifurcated to extend into the iliac arteries.

As discussed above, by forming high metal to vessel ratio stent 100 to have a high metal to vessel ratio, branch vessels 1408, 1410 are adequately perfused through high metal to vessel ratio stent 100 while at the same time tissue ingrowth of main vessel 1404 into high metal to vessel ratio stent 100 is encouraged.

FIG. 17 is a cross-sectional view of the vessel assembly of FIG. 16 illustrating tissue 1702 ingrowth into high metal to vessel ratio stent 100. For example, FIG. 17 illustrates ingrowth of tissue 1702 after a period of time, e.g., weeks or months, after the deployment of high metal to vessel ratio stent 100 into main vessel 1404.

Referring now to FIGS. 16 and 17 together, once deployed, high metal to vessel ratio stent 100 includes a fixation region 1704 and a perfusion region 1706. Fixation region 1704 is the region of high metal to vessel ratio stent 100 in direct contact with main vessel 1404. Perfusion region 1706 is the region of high metal to vessel ratio stent 100 covering ostium 1422 of branch vessel 1408 and covering ostium 1424 of branch vessel 1410.

After deployment of high metal to vessel ratio stent 100, tissue 1702 of main vessel 1404 grows through holes 110 of fixation region 1704 of high metal to vessel ratio stent 100. Tissue 1702 encases, sometimes called encloses or encapsulates, material 108 of fixation region 1704 of high metal to vessel ratio stent 100.

This ingrowth of tissue 1702 provides secure fixation and sealing of high metal to vessel ratio stent 100 to main vessel 1404. By providing secure fixation and sealing of high metal to vessel ratio stent 100 to main vessel 1404, the risk of endoleaks into aneurysm 1406 and migration of high metal to vessel ratio stent 100 is minimized. Further, the ingrowth of tissue 1702 restricts expansion of aneurysm 1406. In one embodiment, aneurysm 1406 is remodeled and essentially eliminated as illustrated in FIG. 17.

Further, as illustrated in FIG. 17, tissue 1702 does not grow over perfusion region 1706 of high metal to vessel ratio stent 100. More particularly, blood flows as indicated by the arrows 1708 through holes 110 of perfusion region 1706 to perfuse branch vessels 1408, 1410. Further, this blood flow prevents tissue overgrowth on perfusion region 1706 thus avoiding occlusion of branch vessels 1408, 1410 and the associated complications.

In one embodiment, to encourage tissue ingrowth, high metal to vessel ratio stent 100 includes a surface treatment. Illustratively, a thin layer of metal is applied, e.g., by sputtering, physical vapor deposition (PVD), plasma enhanced chemical vapor deposition (PECVD), or other application technique, to high metal to vessel ratio stent 100 to encourage tissue ingrowth.

Examples of suitable metals include gold, stainless steel, titanium oxide, and/or copper, or combinations thereof are applied to high metal to vessel ratio stent 100 to encourage tissue ingrowth.

In another embodiment, the surface treatment includes roughening the surface of high metal to vessel ratio stent 100 to encourage tissue ingrowth. For example, the surface is roughened to have a roughness average (RA) of greater than 1.0 micron (μm). The surface can be roughened by plasma etching, laser etching, sandblasting, a selective etch to preferentially etch one component of high metal to vessel ratio stent 100 over another, or other surface roughening technique.

In yet another embodiment, the surface treatment includes a growth factor applied to high metal to vessel ratio stent 100 to enhance tissue ingrowth into high metal to vessel ratio stent 100. Examples of growth factors include vascular endothelial growth factor (VEGF), platelet-derived growth factor (PDGF), plated-derived epidermal growth factor (PDEGF), fibroblast growth factors (FGFs), basic fibroblast growth factor (bFGF), transforming growth factor-beta (TGF-.beta.), platelet-derived angiogenesis growth factor (PDAF) and autologous platelet gel (APG).

Another example of growth factors include bioactive materials, e.g., a bioactive compound, drug, therapeutic agent or composition having a biological effect in an animal. Bioactive materials include small molecules, peptides, proteins, hormones, DNA or RNA fragments, genes, cells, genetically-modified cells, cell growth promoting compositions, inhibitors of matrix metalloproteinase, fatty acids and autologous platelet gel.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A prosthesis comprising:
a plurality of serpentine rings comprising struts;
fingers protruding from the struts, wherein a metal to vessel ratio of the prosthesis when in a final configuration is within the range of 30 percent to 80 percent such as to encourage tissue ingrowth around the prosthesis while allowing perfusion of a branch vessel through walls the prosthesis.

2. The prosthesis of claim 1 wherein the metal to vessel ratio is within the range of 35 percent to 60 percent.

3. The prosthesis of claim 1 wherein the serpentine rings comprise proximal apexes, distal apexes, and struts connecting the proximal apexes and the distal apexes.

4. The prosthesis of claim 3 wherein each proximal apex has two respective struts extending therefrom.

5. The prosthesis of claim 4 wherein, with respect to a proximal apex, each strut comprises an exterior radial surface and an interior radial surface.

6. The prosthesis of claim 5 wherein the exterior radial surface is outward to the interior radial surface in a circumferential direction with respect to the proximal apex.

7. The prosthesis of claim 5 wherein the fingers comprise knuckles and tips, the knuckles being directly attached to the struts.

8. The prosthesis of claim 5 wherein each strut comprises the fingers on both the exterior radial surface and the interior radial surface.

9. The prosthesis of claim 8 wherein a pattern of the fingers on an interior radial surface of a first strut of the two respective struts of the proximal apex is the same as the pattern of fingers on an exterior radial surface of a second strut of the two respective struts of the proximal apex.

10. The prosthesis of claim 8 wherein a pattern of the fingers on an interior radial surface of a first strut of the two respective struts of the proximal apex is different than, and interdigitated with, the pattern of fingers on an interior radial surface of a second strut of the two respective struts of the proximal apex.

11. The prosthesis of claim 1 wherein the proximal apexes of the serpentine rings are directly connected to the distal apexes of the adjacent proximal serpentine ring.

12. The prosthesis of claim 1 further comprising:
a surface treatment to encourage the tissue ingrowth.

13. The prosthesis of claim 12
wherein the surface treatment comprises a metal.

14. The prosthesis of claim 12
wherein the surface treatment comprises roughening the prosthesis.

15. The prosthesis of claim 12 wherein the surface treatment comprises a growth factor.

16. A prosthesis comprising:
a plurality of serpentine rings comprising proximal apexes and distal apexes;
projections projecting from the proximal apexes and the distal apexes, wherein the projections comprise stems and petals.

17. The prosthesis of claim 16 wherein a metal to vessel ratio of the prosthesis when in a final configuration is within the range of 30 percent to 80 percent such as to encourage tissue ingrowth around the prosthesis while ensuring perfusion of a branch vessel through walls of the prosthesis.

18. The prosthesis of claim 16 wherein the stems comprise serpentine ring attachment ends directly connected to the proximal apexes and the distal apexes.

19. The prosthesis of claim 18 wherein the stems further comprise petal attachment ends, the petals being directly attached to the petal attachment ends.

20. The prosthesis of claim 16 wherein each projection comprises two petals.

21. The prosthesis of claim 16 wherein the petals are located in a circumferential direction between directly adjacent apexes of a serpentine ring.

22. The prosthesis of claim 16 wherein the projections further comprise fingers on the stems.

23. The prosthesis of claim 16 wherein the proximal apexes of the serpentine rings are connected to the distal apexes of the adjacent proximal serpentine rings by serpentine ring connectors.

24. The prosthesis of claim 23 wherein the serpentine ring connectors extend in a longitudinal direction.

25. The prosthesis of claim 23 wherein the petals are located in a circumferential direction between directly adjacent serpentine ring connectors.

26. A prosthesis comprising:
a plurality of serpentine rings;
serpentine ring connectors connecting the serpentine rings to one another, wherein a metal to vessel ratio of the prosthesis when in the final configuration is within the range of 30% to 80% such as to encourage tissue ingrowth around the prosthesis while allowing perfusion of a branch vessel through walls of the prosthesis.

27. The prosthesis of claim 26 wherein a thickness of the serpentine rings is greater than a thickness of the serpentine ring connectors.

28. The prosthesis of claim 26 wherein the serpentine ring connectors are welded to the serpentine rings.

29. The prosthesis of claim 26, wherein in the metal to vessel ratio is within the range of 35% to 60%.

* * * * *